United States Patent [19]
Xie

[11] Patent Number: 6,149,644
[45] Date of Patent: Nov. 21, 2000

[54] METHOD AND APPARATUS FOR EPIDERMAL TREATMENT WITH COMPUTER CONTROLLED MOVING FOCUSED INFRARED LIGHT

[75] Inventor: Ping Xie, San Jose, Calif.

[73] Assignee: Altralight, Inc., Sunnyvale, Calif.

[21] Appl. No.: 09/024,437

[22] Filed: Feb. 17, 1998

[51] Int. Cl.[7] .................................................. A61B 18/18
[52] U.S. Cl. ..................... 606/9; 606/3; 606/10; 606/18
[58] Field of Search ................... 606/2, 3, 4, 5, 606/10, 11, 9, 13, 16–18; 607/88, 89

[56] References Cited

U.S. PATENT DOCUMENTS

| | | | |
|---|---|---|---|
| 4,587,396 | 5/1986 | Rubin | 219/121 |
| 5,411,502 | 5/1995 | Zair | 606/10 |
| 5,480,396 | 1/1996 | Simon et al. | 606/4 |
| 5,599,340 | 2/1997 | Simon et al. | 606/4 |
| 5,653,706 | 8/1997 | Zavislan et al. | 606/9 |
| 5,782,822 | 7/1998 | Telfair et al. | 606/5 |
| 5,885,273 | 3/1999 | Eckhouse et al. | 606/9 |
| 5,885,274 | 3/1999 | Fullmer et al. | 606/9 |
| 5,957,915 | 9/1999 | Trost | 606/13 |
| 5,971,978 | 10/1999 | Mukai | 606/18 |
| 6,010,497 | 1/2000 | Tang et al. | 606/5 |

*Primary Examiner*—Linda C. M. Dvorak
*Assistant Examiner*—Bryan K. Yarnell
*Attorney, Agent, or Firm*—Pacific Law Group, LLP; Chi Ping Chang

[57] ABSTRACT

A method and apparatus for treating the epidermis with actinic light includes a solid state diode system with a continuous output. The light beam is generated by either a high power light emitting diode or a laser diode or a combination thereof. A computer controlled pattern generator (CCPG) directs the continuous light beam to trace predetermined patterns on a selected area of the skin. This integrated continuous light source and patterned treatment technique obviate the need for high peak power pulsed systems, while providing sufficient energy density at the target site to effect hair removal and other skin treatment modalities. The moving light beam has a computer controlled dwell time to generate a relatively high amount of energy in a short period of time at the target. The optimum dwell time is about 0.5 ms to 500 ms, and the wavelength is in the range of 600 nm to 990 nm. The spot size is in the range of 0.01 to 10.0 mm and the treatment area is in the range of 0.01 to 100 cm$^2$. The CCPG patterns enable the moving focal spot of light to irradiate all of the treatment area uniformly with minimum overlap. The patterns may comprise regular geometric forms, or may comprise non-uniform random patterns. In either case, focal spot movement is controlled to avoid excessive irradiation of any point within the treatment area, and avoid localized temperature buildup that can occur when the spot is retraced too often through the same locality.

20 Claims, 6 Drawing Sheets

METHOD AND APPARATUS FOR EPIDERMAL TREATMENT WITH COMPUTER CONTROLLED MOVING FOCUSED INFRARED LIGHT

BACKGROUND OF THE INVENTION

There has been significant interest in developing laser systems or other light sources for removing unwanted hair from human skin, and treatment of pigmented lesions and vascular lesions. A variety of types of surgical laser systems and light sources have been developed for these applications, as well as for treating skin conditions such as port wine stains, varicose veins, and the like. These systems can be divided into several classifications, either high power, pulsed, solid state laser systems, pulsed coherent light systems, or high power pulsed flash lamp light sources.

The most effective laser systems are developed to deliver a relatively high amount of energy in a short period of time. If the energy is delivered over a long period of the time, significant tissue injury (collateral damage) will occur in the regions adjacent to or beneath the treated area. To avoid this problem and generate higher power in a short period of the time, most prior art systems are flash lamp pumped laser systems having a pulsed output. In U.S. Pat. No. 5,059,129, issued Oct. 22, 1991, to Zaias, a flash lamp pumped ruby laser system is disclosed. In U.S. Pat. No. 5,423,803, issued Jan. 13, 1995, Tankorich describes a flash lamp pumped Nd:YAG laser used in combination with the application of a substance having a high absorption at the laser wavelength for depilation. In U.S. Pat. No. 5,405,368, issued Apr. 11, 1995, Eckhose disclosed a non-coherent light source comprised of a high power pulsed flash lamp with a wavelength from 500 nm to 900 nm for removing unwanted hair from human skin. In U.S. Pat. Nos. 5,630,811 and 5,658,323, issued to Miller, a method and apparatus to use a high peak power pulsed laser diode light with wavelength in the range 650–1000 nm has been disclosed for treatment of pigmented lesions and vascular lesions and hair removal. All these high energy pulsed laser systems and non-coherent light source require a very high energy pulsed power supply, which in turn requires a larger cooling system. Normally these types of laser systems and non-coherent light sources are heavy, large, expensive and very difficult to use in a clinical office.

SUMMARY OF THE INVENTION

The present invention generally comprises a low cost, small size and light weight solid state diode system with a continuous output for hair depilation and treatment of pigmented lesions and vascular lesions. The light beam is generated by a semiconductor device comprising either a high power light emitting diode or a laser diode or a combination of such devices. The output is fed to a computer controlled pattern generator (CCPG). The CCPG directs the continuous light beam to trace predetermined patterns on a selected area of the skin to be treated. This integrated continuous light source and patterned treatment technique obviate the need for high peak power pulsed systems, while providing sufficient energy density at the target site to effect hair removal and other skin treatment modalities.

A significant aspect of the CCPG is that the moving light beam has a computer controlled "dwell time" to generate a predetermined relatively high amount of energy in a short period of time at the target. In order to minimize the thermal damage to the surrounding tissue, the optimum "dwell time" is designed to be about 0.5 ms to 500 ms, depending upon the size and color of human hair. The wavelength is in the range of 600 nm to 990 nm. This wavelength is absorbed most efficiently in the hair follicles, and less efficiently in the surrounding epidermis. Upon receiving the light energy from the invention, the hair follicles are heated, damaged, coagulated and collapsed. Thereafter, the follicles are incapable of producing further hair growth, while the surrounding epidermis is relatively unaffected.

The system of the invention provides a focused light beam with a spot size in the range of 0.01 to 10.0 mm. The computer controlled light patterns irradiate a section of human skin with predetermined patterns, with the treatment area being in the range of 0.01 to 100 cm$^2$.

A significant aspect of the invention is the predetermined patterns that are generated by the CCPG. The patterns are designed to enable the moving focal spot of light to irradiate all of the treatment area uniformly with minimum overlap. The patterns may comprise scan patterns having regular geometric forms, or may comprise non-uniform random patterns. In either case, the computer controlled moving focal spot is directed in such a manner to avoid excessive irradiation of any point within the treatment area, as well as avoiding localized temperature buildup that can occur when the moving spot is retraced too often through the same locality.

One of the objectives of the invention is to provide predetermined scanning patterns with different sizes for different color of the human hair and treatment of pigmented lesions and vascular lesions.

Another objective of the invention is to provide predetermined scanning patterns with different pattern shapes for different area of the human hair and treatment of pigmented lesions and vascular lesions.

A further objective of the invention is to provide predetermined scanning patterns with different line scanning density and overlaps for different color of the human hair and treatment of pigmented lesions and vascular lesions.

The invention further includes the methodology embodied in using the system of the invention for depilation and treatment of other skin conditions.

DESCRIPTION OF THE PREFERRED EMBODIMENT

Figure 1:
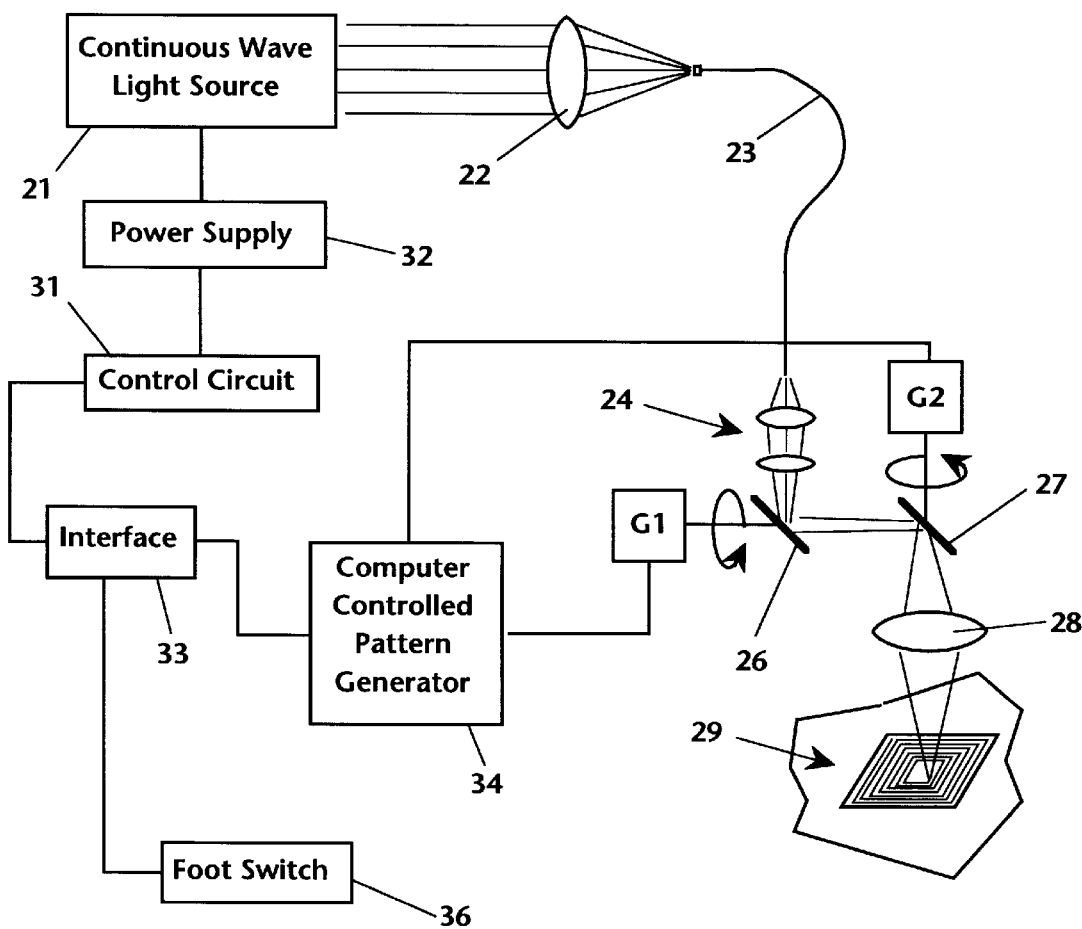
FIG. 1 is a functional block diagram of the apparatus of the invention for generating and directing a moving light spot on skin for treating a defined area in a predetermined pattern.

The present invention generally comprises a method and apparatus for generating and scanning a continuous light spot on a defined portion of the epidermis to achieve a desired treatment modality such as depilation, tattoo removal, and reduction of vascular lesions and pigmented lesions. With regard to FIG. 1, the apparatus of the invention generally includes a continuous wave light source 21, such as a laser diode, high power light emitting diode, or similar efficient, controllable semiconductor light generator. The wavelength of the light source 21 is in the range of 600–900 nm, and the power output is in the range of 0.5–600 watts. To achieve this power level, it may be necessary to couple a plurality of semiconductor light generators, as is known in the prior art. The output of the light source 21 is focused by lens 22 to be inserted into a light conductor 23, such as an optical fiber, light pipe, or the like.

The output of the light conductor 23 is delivered to a collimating lens system 24, which in turn directs the light output to a movable mirror 26. The light reflected from mirror 26 is directed to movable mirror 27, which in turn directs the light output through a focusing lens 28 to form a beam scanning pattern 29 on the epidermis of a patient. Mirror 26 is selectively rotated by galvanometer G1, and mirror 27 is selectively rotated by galvanometer G2, the rotational axes of the two mirrors being non-parallel and, preferably, orthogonal. The combined effect of the mirrors 26 and 27 is to form a movable focal spot on the epidermis, and the galvanometers G1 and G2 enable precise movement of the focal spot in a predetermined pattern 29, as will be explained in the following description. The size of the focal spot is in the range of 0.01–10.0 mm, and the area of the pattern 29 is in the range of 0.01 to 100 cm$^2$. The spot size is selected in accordance with the power of the light output delivered to the epidermis to achieve a power density sufficient to effect the desired treatment, and the relationship of these parameters is known in the prior art. These factors are also related to the velocity of movement of the focal spot on the epidermis, whereby the spot is provided with sufficient dwell time at each incremental point of the scan pattern 29 to accomplish the desired effect, whether depilation, coagulation, ablation, or the like. The range of dwell time is 0.5–500 msec, depending on the power output of the light source, the pigment of the skin, the color of the hair (for depilation), and similar factors.

The apparatus further includes a power supply 32 that is connected to drive the light source 21, and also to selectively interrrupt the continuous output thereof. A control circuit 31 is connected to operate the power supply 32, and is also connected through an interface 33 to a computer controlled pattern generator 34, hereinafter CCPG. A foot switch 36 is also connected to the interface 33 to permit start/stop operator control of the system. The CCPG 34 is connected to galvanometers G1 and G2, and is designed to generate galvanometer control signals that provide precise angular control of the galvanometers in real time to rotate mirrors 26 and 27 and define any one of a plurality of scanning patterns 29. The CCPG 34 may generate x-y coordinates for the moving spot, and increment the x-y coordinates as required to form a desired pattern. The CCPG 34 may also establish a list of coordinates that have been irradiated by the moving spot, whereby further irradiation of these points may be blocked, either by preventing movement of the spot to these points or by blanking the power supply 32 as the moving spot traverses these points, as will be explained in the following description.

Figure 2A:
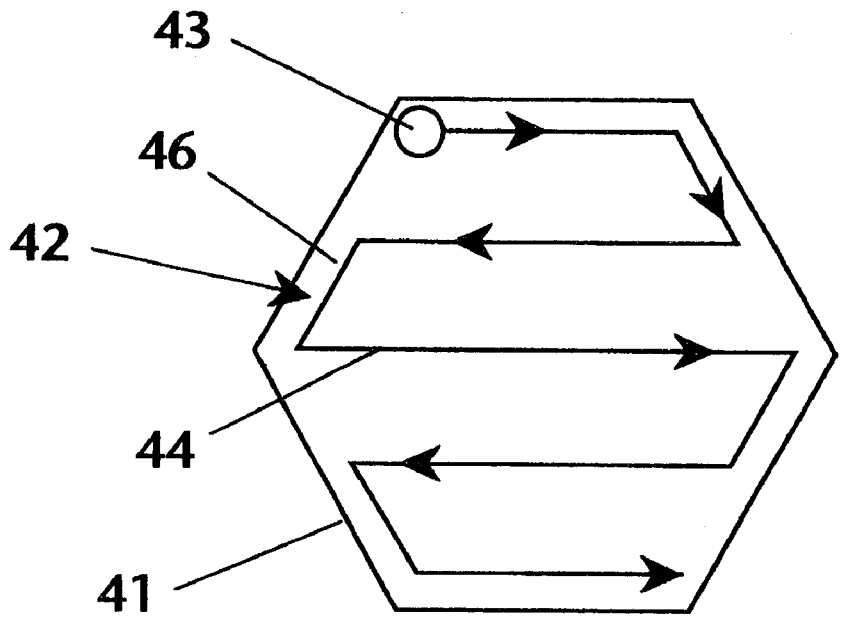
FIG. 2A and 2B are sequential schematic representations of a continuous light spot scan pattern of the invention for treatment of a defined area of the skin.

The spot scanning patterns developed by the CCPG 34 are designed to apply an average power density to the area of treatment that is generally uniform throughout the treatment area. With regard to FIG. 2A, the CCPG 34 may define a treatment area within a regular geometric shape, such as a hexagon 41. Other regular or irregular closed geometric shapes, such as circles, ellipses, rectangles, triangles, pentagons, septagons, octogons, and the like may be employed with equal effect. The galvanometers G1 and G2 are driven in combination to cause the actinic light spot to move in a scan pattern 42 that begins at starting point 43 and proceeds to scan parallel, spaced apart lines 44 that are joined by connecting legs 46 in a continuous fashion. The lines 44 are parallel to one of the sides of the hexagon 41, and the scan proceeds from line to line across the width of the geometric figure to the opposed side. The velocity of the movement of the actinic spot along the continuous scan path is generally constant.

Figure 2B:
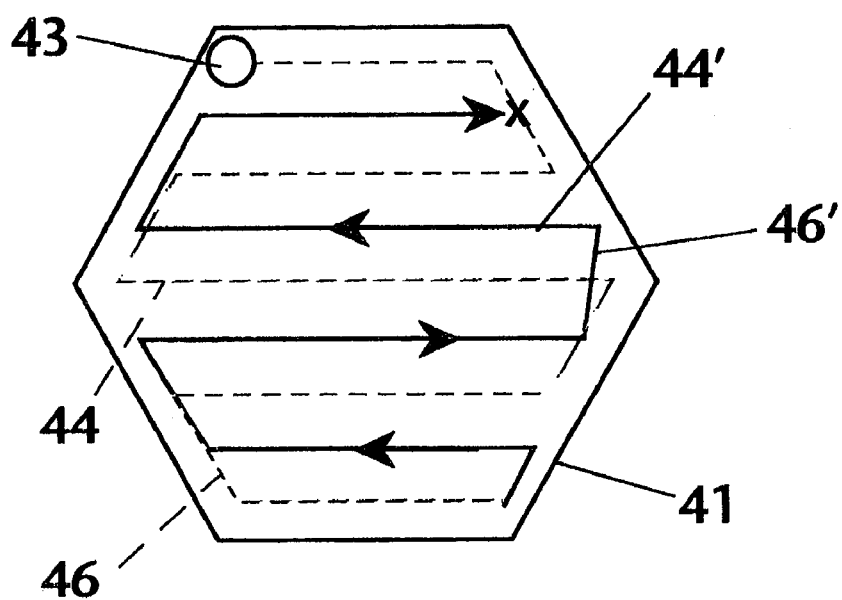

Referring to FIG. 2B, as the moving spot reaches the opposed side of the hexagon 41, it then begins to scan parallel lines 44' disposed in the spaces between the lines 44, the lines 44' being joined by connecting legs 46' in continuous fashion. The scan proceeds to return toward the side of the FIG. 41 where in began, and the scan ends at point X. The spacing of lines 44 and 44' is dimensioned so that the moving spot overlaps it previous adjacent traces sufficiently to provide a uniform power density throughout the FIG. 41. The amount of overlap is in the range of ±90%, and is precisely controlled in 10% increments. The interleaved scan lines aid in preventing unacceptable temperature increases in the epidermis by providing an off-time, or cooling period, that can be varied from 0 to 5 seconds by selecting line spacing, spot velocity, and size and shape of the geometric area 41.

Figure 3A:
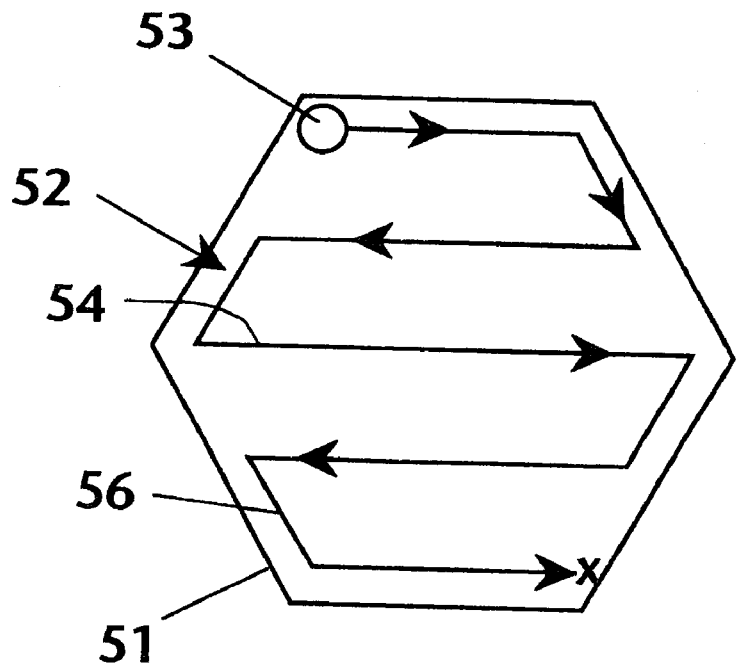
FIG. 3A and 3B are sequential schematic representations of another continuous light spot scan pattern of the invention for treatment of a defined area of the skin.
Figure 3B:
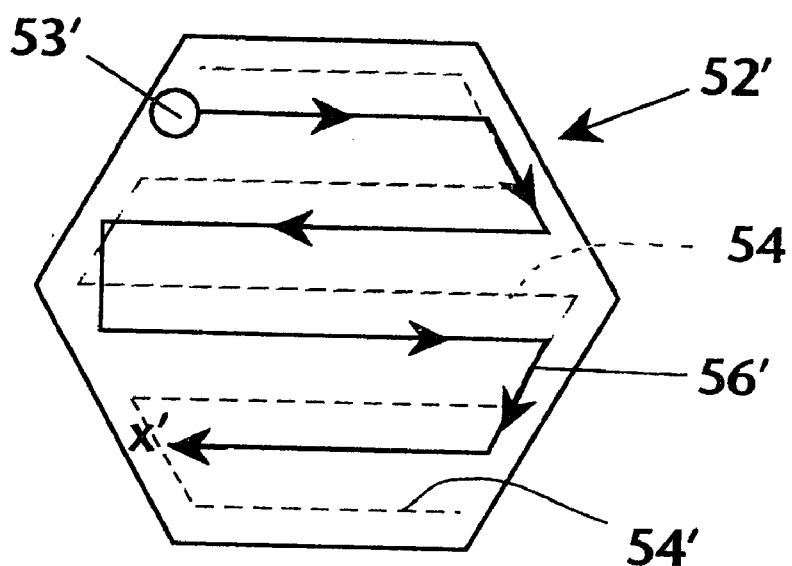

With regard to FIGS. 3A and 3B, the methodology of the invention further includes a technique in which a treatment area 51 is scanned by a pattern 52 that begins at starting point 53 and proceeds to scan parallel, spaced apart lines 54 that are joined by connecting legs 56 in a continuous pattern. As before, the lines are parallel to one side of the FIG. 41, and the scan proceeds from line to line across the width of the FIG. 41. However, in the technique of FIGS. 3A and 3B, the scan ends at point X adjacent to the side of the figure opposed to the starting side. Thereafter, a second continuous scan pattern 52' is initiated, beginning at point 53' and following lines 54' and connector legs 56', the lines 54' being interleaved between the lines 54 of the first scan pattern 52. The scan 52' ends at point X', whereby the geometric FIG. 51 has been filled with scan lines that permit the actinic spot to irradiate the entire area of the figure generally uniformly with sufficient fluence to achieve the desired effect, whether depilation, coagulation, ablation, or the like. This technique may be reiterated using adjacent parallel scans; i.e., three or more parallel scans 52" may be interleaved within the perimeter 51 to fill the area therein with scan lines. As in the scan technique depicted in FIGS. 2A and 2B, this technique provides complete coverage and uniform irradiation of the area within the FIG. 51, while also providing sufficient cooling time, dwell time, and power density delivered to the epidermis.

Figure 4C:
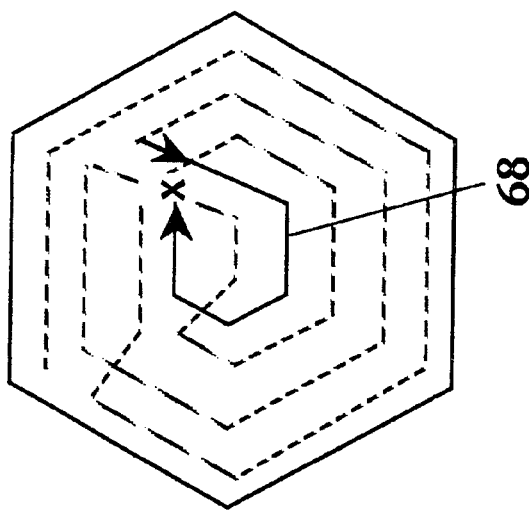
FIG. 4A–4C are sequential schematic representations of a further continuous light spot scan pattern for treatment of a defined area of the skin.
Figure 4B:
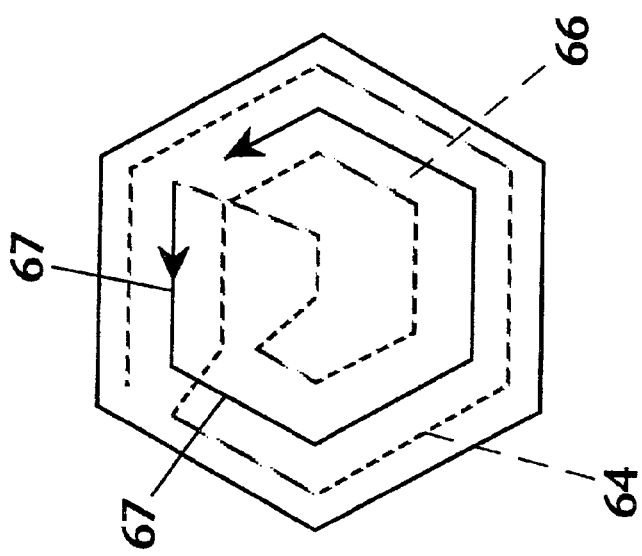
Figure 4A:
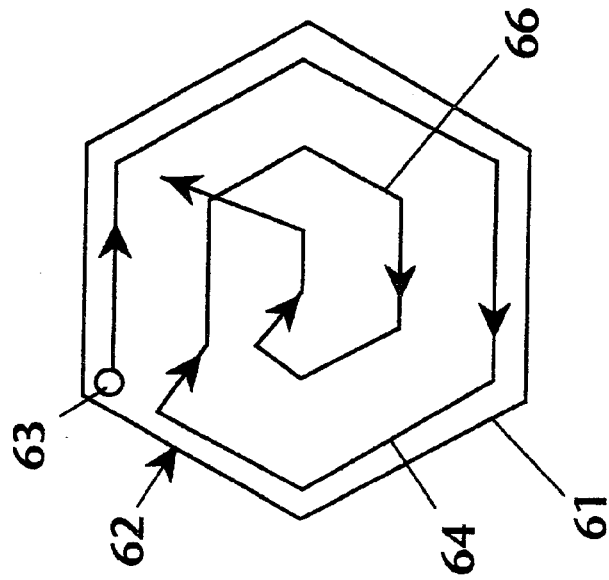

With reference to FIGS. 4A–4C, another scan technique of the invention is also carried out within a defined treatment area 61, here again illustrated as a hexagon. The scan begins at starting point 63 and proceeds clockwise along a path 64 closely adjacent and parallel to the perimeter sides until it approaches returning to the starting point 63. Thereafter the scan path moves inwardly toward a medial portion of the area 61, and traces a path 66 that extends clockwise generally parallel to and concentric within the path 64. After one clockwise cycle, the path 66 extends outwardly to a point midway between the previous paths 64 and 66, and then proceeds along path 67 counterclockwise therebetween (FIG. 4B). The scan path then is directed inwardly once again to path 68, where it moves clockwise again in another cycle concentrically within path 66 to an end point X. Although this path is tortuous in description, it enables complete coverage of the area 61 in one continuous scan.

Figure 5:
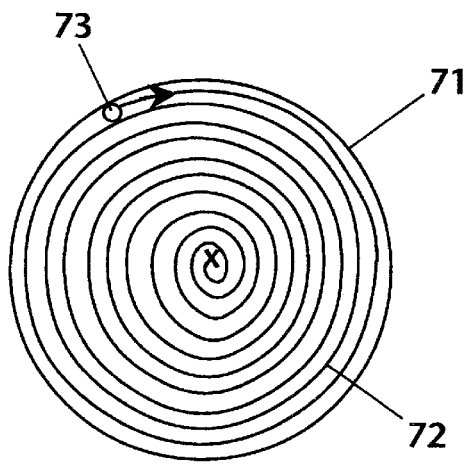
FIG. 5 is a schematic representation of another continuous light spot spiral scan pattern for treatment of a defined area of the skin.

A simpler scan format, shown in FIG. 5, involves a defined treatment area 71 having a circular configuration. The scan path 72 begins at starting point 73 adjacent to the perimeter, and follows a spiral course in repeated cycles within the circle, until it arrives at the end point X at the center of the circle. As in previous patterns, the scan line spacing is selected to permit a desired degree of line overlap which provides the necessary average power density throughout the area 71 to achieve the desired treatment effect.

Figure 6:
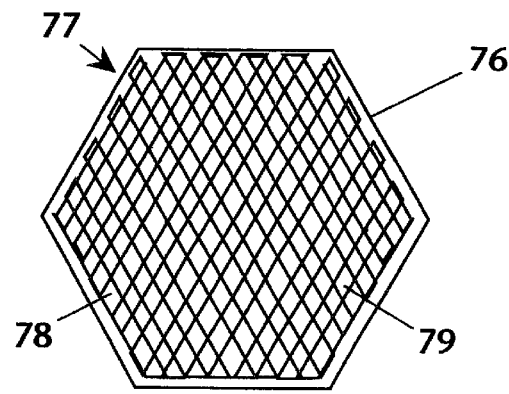
FIG. 6 is a schematic representation of another continuous light spot intersecting raster scan pattern for treatment of a defined area of the skin.

With regard to FIG. 6, another scan technique is carried out within treatment area 76, again depicted as a hexagon. The scan path 77 comprises a first set of spaced apart parallel lines 78 disposed parallel to one side of the hexagon and extending the width of the area. The lines 78 are joined at adjacent ends to form a continuous path across the treatment area. The scan path 77 also includes a second set of spaced apart parallel lines 79 disposed parallel to another side of the hexagon and intersecting the first set 78. The two sets of lines create a large plurality of intersections and overlaps, whereby a high power density may be applied to the treatment area 76.

Figure 7:
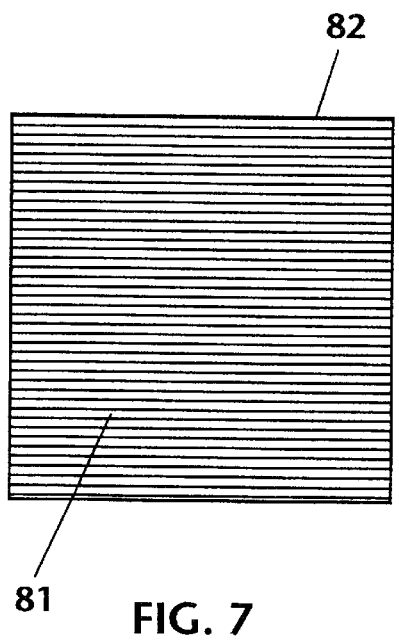
FIG. 7 is a schematic representation of a further continuous light spot raster scan pattern for treatment of a defined area of the skin.

The CCPG 34 may also be programmed to create a raster scan path 81 within a rectangular area 82 as shown in FIG. 7. The raster scan, well known in the electronic display art, comprises an array of parallel lines that fills the area 82 with sufficient density to irradiate the epidermis with the desired power density.

Figure 8:
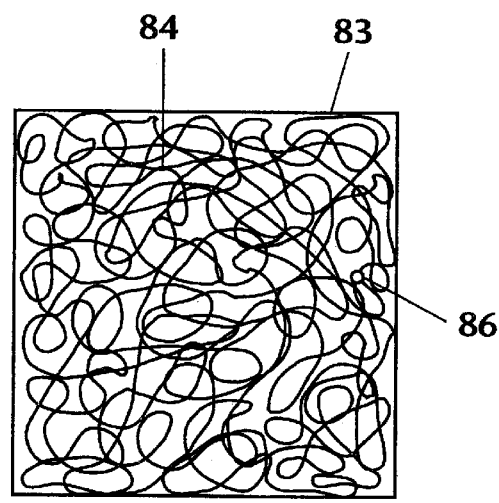
FIG. 8 is a schematic representation of a continuous light spot pseudo-random scan pattern for treatment of a defined area of the skin.

With regard to FIG. 8, a unique format for scanning an area 83 of any perimetrical configuration comprises a scan path 84 that is entirely random. The CCPG 34 generates random or pseudo-random numbers that incrementally redirect the scan path without regard to any planned format. Beginning at starting point 86, the path 84 follows a tortuous random pattern that will fill the area 83 in a generally uniform manner within a statistically predictable time period. Furthermore, the CCPG 34 stores addresses of incremental points that have been irradiated, and these points may be excluded from the random movement, whereby a pseudo-random movement is directed toward areas that require irradiation.

Figure 9:
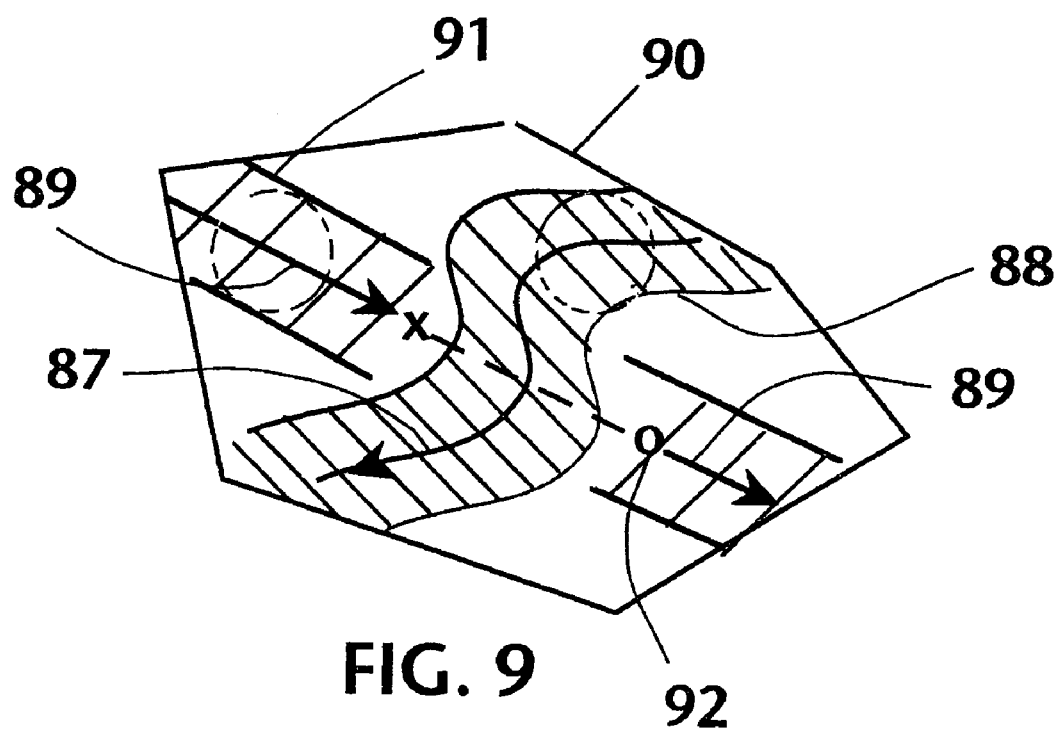
FIG. 9 is an enlarged detailed schematic representation of a scan technique for avoiding intersecting scan lines in a continuous light spot scan pattern for treatment of a defined area of the skin.

For example, with regard to FIG. 9, a portion of a scan path 87 irradiates a swath 88 within an incremental area 90 undergoing treatment. The addresses of all treatment points along path 87 are stored in the CCPG 34. Subsequently, another scan path 89, which irradiates a swath 91, approaches the previous path 87. As the path 89 attains a predetermined minimum distance from the swath 88, the actinic beam is interrupted at point X , thereby avoiding repeated irradiation of the intersecting swaths 91 and 88. Thereafter, the actinic beam of scan path 89 is resumed at point 92, and the scan pattern proceeds at described above.

The technique depicted in FIG. 9 for avoiding excessive irradiation of tissue may be applied not only to the random scan pattern depicted in FIG. 8, but also to other scan techniques described herein, such as those shown in FIGS. 2, 3, 4, and 6.

The foregoing description of the preferred embodiment of the invention has been presented for purposes of illustration and description. It is not intended to be exhaustive or to limit the invention to the precise form disclosed, and many modifications and variations are possible in light of the above teaching without deviating from the spirit and the scope of the invention. The embodiment described is selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

What is claimed is:

1. An apparatus for irradiating a target tissue within an area below the epidermis to cause selective, thermo-kinetic coagulation of said target tissue without causing ablation of a non-target tissue within said area, said apparatus comprising:

means for generating a continuous, high intensity light beam having a wavelength in the range of 600 nm to 990 nm to be selectively and thermokinetically absorbed by said target tissue;

means for directing said light beam to a focal spot on said area;

a scanning means for moving said focal spot in a predetermined pattern within said area so that said target tissue and said non-target tissue within said area is non-sequentially and non-continuously irradiated; and means for controlling said scanning means to move said focal spot according to said predetermined pattern in said non-sequential and non-continuous manner such that the coagulation of said target tissue is achieved without causing any ablation to said non-target tissue.

2. The apparatus of claim 1, wherein said means for scanning includes a computer controlled pattern generator.

3. The apparatus of claim 2, wherein said means for directing includes first and second mirrors, said first mirror disposed to receive said light beam from said means for generating, and said second mirror disposed to receive said light beam from said first mirror and direct said light beam toward the epidermis.

4. The apparatus of claim 3, wherein said means for scanning includes first means for rotating said first mirror about a first axis in an incremental, controlled fashion, and second means for rotating said second mirror about a second axis in an incremental, controlled fashion, whereby said focal spot is moved within said predefined area on the epidermis.

5. The apparatus of claim 4, wherein said means for scanning includes a computer controlled pattern generator means for selectively actuating said first and said second means for rotating.

6. The apparatus of claim 5, wherein said computer controlled pattern generator means includes means for establishing a dwell time for said focal spot, said dwell time ranging from 0.5 ms to 500 ms.

7. The apparatus of claim 5, wherein said computer controlled pattern generator means includes means for controlling said first and second means for rotating to direct said focal spot along a predetermined path within said predefined area.

8. The apparatus of claim 7, wherein said predetermined path comprises a continuous spiral trace filling said predefined area.

9. The apparatus of claim 7, wherein said predetermined path includes a plurality of path portions, said plurality of path portions extending in spaced apart fashion.

10. The apparatus of claim 9, wherein said plurality of path portions define a raster scan within said predefined area.

11. The apparatus of claim 9, wherein a first path portion comprises a first trace extending continuous in a geometric pattern within said predefined area, and at least one further trace extending continuously and interleaved with said geometric pattern.

12. The apparatus of claim 11, wherein said computer controlled pattern generator disposes said first trace and said at least one further trace to establish a tissue cooling time in the range of 0–5 seconds.

13. The apparatus of claim 9, wherein said predetermined path includes a first raster scan filling said predefined area, and a second raster scan filling said predefined area and intersecting said first raster scan.

14. The apparatus of claim 9, further including means for blanking said means for generating a continuous high intensity light beam when one of said plurality of path portions intersects another of said plurality of path portions.

15. The apparatus of claim 9, wherein said computer controlled pattern generator means includes means for establishing a predetermined overlap of adjacent segments of said plurality of path portions.

16. The apparatus of claim 15 wherein said predetermined overlap of said plurality of path portions is in the range of ±90%, and variable in increments of 10%.

17. The apparatus of claim 1, wherein said focal spot has a diameter in the range of 0.01 mm to 10.0 mm.

18. The apparatus of claim 1, wherein the size of said predefined area is in the range of 0.01 $cm^2$ to 100 $cm^2$.

19. The apparatus of claim 1, wherein said light beam has a power in the range of 0.5 to 500 watts.

20. A method for irradiating a target tissue within an area below the epidermis to cause selective, thermo-kinetic coagulation of said target tissue without causing ablation of a non-target tissue within said area, comprising the steps of:

directing a continuous wave, high intensity light beam having a wavelength in the range of 600 nm to 990 nm toward the area to be selectively and thermo-kinetically absorbed by said target tissue;

scanning said light beam in a predetermined pattern within said area to provide sufficient irradiation to said area; and controlling said light beam to move according to said predetermined pattern in non-sequential and non-continuous manner such that the coagulation of said target tissue is achieved without causing any ablation to said non-target tissue.

\* \* \* \* \*